United States Patent
Maeno et al.

(10) Patent No.: US 9,606,041 B2
(45) Date of Patent: Mar. 28, 2017

(54) PARTICLE ADSORPTION PROBE

(71) Applicant: Nitto Denko Corporation, Ibaraki-shi, Osaka (JP)

(72) Inventors: Youhei Maeno, Ibaraki (JP); Akiko Toyokawa, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 172 days.

(21) Appl. No.: 14/390,429

(22) PCT Filed: Apr. 9, 2013

(86) PCT No.: PCT/JP2013/060664
§ 371 (c)(1),
(2) Date: Oct. 3, 2014

(87) PCT Pub. No.: WO2013/157435
PCT Pub. Date: Oct. 24, 2013

(65) Prior Publication Data
US 2015/0040690 A1    Feb. 12, 2015

(30) Foreign Application Priority Data
Apr. 19, 2012  (JP) ................... 2012-095414

(51) Int. Cl.
*G01N 1/02*  (2006.01)
*B25J 7/00*  (2006.01)
(Continued)

(52) U.S. Cl.
CPC ............ *G01N 15/10* (2013.01); *B01L 3/0289* (2013.01); *G01N 1/04* (2013.01);
(Continued)

(58) Field of Classification Search
CPC .... B25J 7/00; G01N 1/02; G01N 1/04; G01N 15/10; G01N 2001/028; G01N 2001/2826;
(Continued)

(56) References Cited

U.S. PATENT DOCUMENTS 7,066,513 B2 *  6/2006  Yamanaka ................ B82B 3/00
                                                        294/86.4
7,261,352 B2    8/2007  Maslov et al.
(Continued)

FOREIGN PATENT DOCUMENTS

CN    102015525 A    4/2011
CN    102358615 A    2/2012
(Continued)

OTHER PUBLICATIONS

Supplementary European Search Report dated Oct. 21, 2015, issued by the European Patent Office in corresponding EP Application No. 13778067.2.
(Continued)

*Primary Examiner* — Nguyen Ha
(74) *Attorney, Agent, or Firm* — Sughrue Mion, PLLC

(57) ABSTRACT

Provided is a novel particle adsorption probe (1000) for picking up a particle by adsorbing the particle. The particle adsorption probe (1000) can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle. The particle adsorption probe (1000) of the present invention includes a carbon nanotube aggregate (100) including a plurality of carbon nanotubes (10).

10 Claims, 4 Drawing Sheets

(51) Int. Cl.
  *G01N 15/10* (2006.01)
  *B01L 3/02* (2006.01)
  *G01N 1/04* (2006.01)
  *G01N 1/28* (2006.01)
  *B82Y 35/00* (2011.01)

(52) U.S. Cl.
  CPC ............ *B01L 2200/0657* (2013.01); *B01L 2300/0838* (2013.01); *B01L 2300/0896* (2013.01); *B82Y 35/00* (2013.01); *C01B 2202/06* (2013.01); *G01N 2001/028* (2013.01); *G01N 2001/2826* (2013.01); *Y10S 977/953* (2013.01)

(58) Field of Classification Search
  CPC .......... B01L 3/0289; B01L 2200/0657; B01L 2300/0838; B01L 2300/0896; B82Y 35/00; Y10S 977/953; C01B 2202/06
  See application file for complete search history.

(56) References Cited

U.S. PATENT DOCUMENTS

| | | | |
|---|---|---|---|
| 8,025,971 | B2 | 9/2011 | Maeno et al. |
| 2002/0084410 | A1 | 7/2002 | Colbert et al. |
| 2002/0158480 | A1* | 10/2002 | Nakayama ............... B25J 7/00 294/99.1 |
| 2002/0182109 | A1* | 12/2002 | Hidaka ............... B82Y 15/00 422/68.1 |
| 2004/0004364 | A1* | 1/2004 | Nakayama ............... B25B 9/02 294/86.4 |
| 2004/0056194 | A1 | 3/2004 | Moore et al. |
| 2005/0244326 | A1 | 11/2005 | Colbert et al. |
| 2005/0269509 | A1* | 12/2005 | Collier ................... B82Y 15/00 250/309 |
| 2006/0076790 | A1 | 4/2006 | Maslov et al. |
| 2008/0105043 | A1* | 5/2008 | Yasutake ................ G01Q 60/30 73/105 |
| 2011/0189459 | A1 | 8/2011 | Maeno et al. |

FOREIGN PATENT DOCUMENTS

| | | |
|---|---|---|
| EP | 2 266 921 A1 | 12/2010 |
| EP | 2 811 293 A1 | 12/2014 |
| JP | 2000-516708 A | 12/2000 |
| JP | WO 0166460 A1 * 9/2001 ................ B25J 7/00 |
| JP | 2006-35418 A | 2/2006 |
| JP | 2006-068830 A | 3/2006 |
| JP | 2006-205271 A | 8/2006 |
| JP | 2008-52232 A | 3/2008 |
| JP | 2011-132075 A | 7/2011 |
| WO | 98/05920 A1 | 2/1998 |
| WO | 2009/128343 A1 | 10/2009 |
| WO | 2013/115145 A1 | 8/2013 |

OTHER PUBLICATIONS

Notification of First Office Action dated Jun. 26, 2015 from the State Intellectual Property Office of the People's Republic of China in counterpart application No. 201320030552.2.

International Search Report for PCT/JP2013/060664 dated Jun. 4, 2013.

* cited by examiner

PARTICLE ADSORPTION PROBE

CROSS REFERENCE TO RELATED APPLICATIONS

This application is a National Stage of International Application No. PCT/JP2013/060664 filed Apr. 9, 2013, claiming priority based on Japanese Patent Application No. 2012-095414 filed Apr. 19, 2012, the contents of all of which are incorporated herein by reference in their entirety.

TECHNICAL FIELD

The present invention relates to a particle adsorption probe, and more specifically, to a particle adsorption probe to be suitably used for, for example, picking up fine particles scattered on a surface of an object to be analyzed in an analysis application or the like so that the particles may be carried into an analysis apparatus and analytically evaluated.

BACKGROUND ART

In order to provide a clean member free of foreign matter, it is important to elucidate, for example, a route through which a member is contaminated with foreign matter in a production process therefor by analytically evaluating, for example, composition or shape of the foreign matter scattered on a surface of the member.

Generally used means for evaluating the composition or shape of the foreign matter scattered on the surface of the member is a particle adsorption probe that uses a tungsten probe or a microknife as a sampling tool. Such particle adsorption probe is used to pick up the foreign matter scattered on the surface of the member with the sampling tool so that the foreign matter may be carried into an analysis apparatus and analytically evaluated for its composition, shape, or the like (see, for example, Patent Literature 1).

However, in order to pick up the foreign matter, the particle adsorption probe that uses a tungsten probe or a microknife as a sampling tool requires application of a physical stress generated by, for example, puncturing the foreign matter with the sampling tool. When such physical stress is applied, a problem arises in that it becomes difficult to observe the raw structure or composition of the surface owing to, for example, detachment of a surface coating material or a change in surface unevenness or layer structure.

Meanwhile, when an adhesive such as a paste or a pressure-sensitive adhesive such as a double-sided tape is used as a sampling tool in order to pick up the foreign matter without applying a physical stress, there arises a problem in that an organic component contained in the adhesive or the pressure-sensitive adhesive contaminates the surface of the foreign matter to prevent accurate analytical evaluation of the foreign matter. In addition, when the adhesive or pressure-sensitive adhesive as described above is used as a sampling tool, it is difficult to selectively pick up a particle having a specific particle diameter from a group of particles having a wide particle diameter distribution.

In addition, when the foreign matter picked up using the related-art particle adsorption probe is carried into an analysis apparatus and analytically evaluated, the foreign matter that has been carried into the analysis apparatus needs to be newly fixed with a paste or the like before the analytical evaluation, which complicates the process.

CITATION LIST

Patent Literature

[PTL 1] JP 2008-52232 A

SUMMARY OF INVENTION

Technical Problem

An object of the present invention is to provide a novel particle adsorption probe for picking up a particle by adsorbing the particle, which can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

Solution to Problem

According to one embodiment of the present invention, there is provided a particle adsorption probe, including a carbon nanotube aggregate including a plurality of carbon nanotubes.

In a preferred embodiment, the particle adsorption probe of the present invention further includes a shaft-shaped base material, in which the carbon nanotube aggregate is provided on the shaft-shaped base material.

In a preferred embodiment, the carbon nanotubes each have a plurality of walls, a distribution width of a wall number distribution of the carbon nanotubes is 10 walls or more, and a relative frequency of a mode of the wall number distribution is 25% or less.

In a preferred embodiment, the carbon nanotubes each have a plurality of walls, a mode of a wall number distribution of the carbon nanotubes is present at 10 or less walls in number, and a relative frequency of the mode is 30% or more.

In a preferred embodiment, the particle adsorption probe of the present invention selectively adsorbs a particle having a diameter of 200 µm or less.

Advantageous Effects of Invention

According to one embodiment of the present invention, the novel particle adsorption probe for picking up a particle by adsorbing the particle, which can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle, can be provided.

DESCRIPTION OF EMBODIMENTS

<<Particle Adsorption Probe>>

A particle adsorption probe of the present invention includes a carbon nanotube aggregate including a plurality of carbon nanotubes. The particle adsorption probe of the present invention preferably includes the carbon nanotube aggregate including a plurality of carbon nanotubes at at least a tip portion thereof. By virtue of including such carbon nanotube aggregate, the particle adsorption probe of the present invention can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

The particle adsorption probe of the present invention may adopt, for example, a construction in which the particle adsorption probe consists only of the carbon nanotube aggregate including a plurality of carbon nanotubes, or a construction in which the carbon nanotube aggregate including a plurality of carbon nanotubes is provided on a shaft-shaped base material. Herein, the shaft-shaped base material means a base material having a shaft shape, and may be alternatively referred to as, for example, shaft, support rod, or metal rod in some cases.

Figure 1:
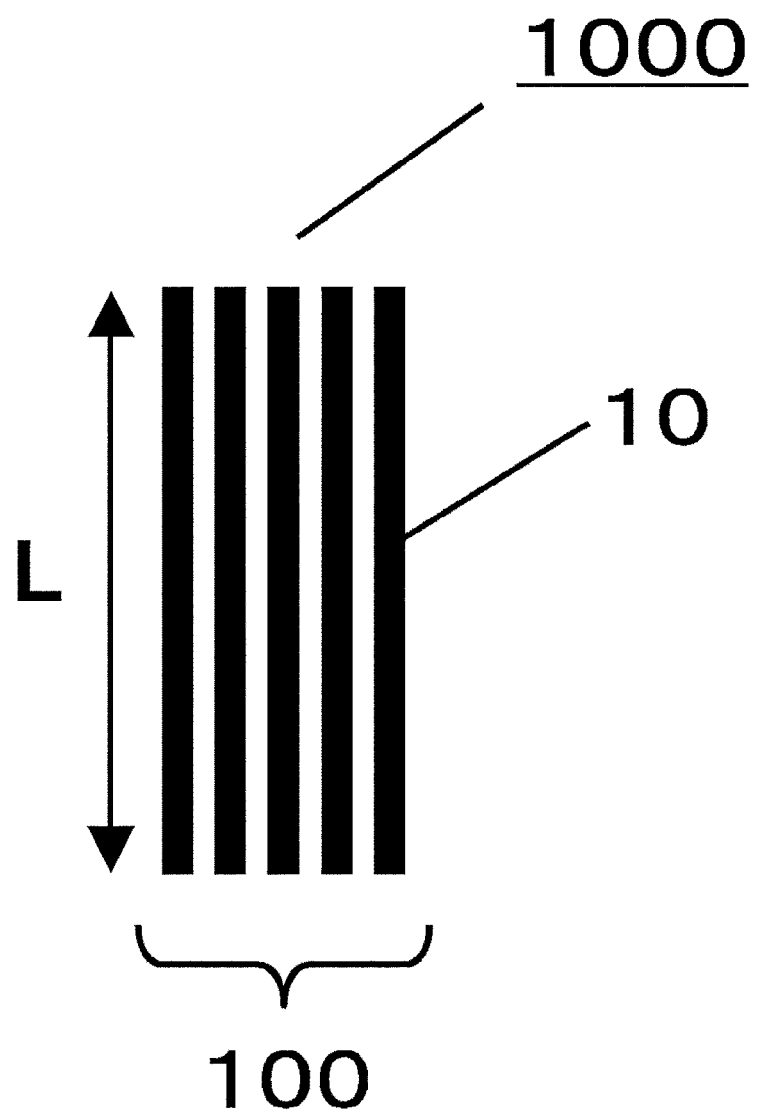
FIG. 1 is a schematic sectional view of an example of a particle adsorption probe in a preferred embodiment of the present invention.

FIG. 1 is a schematic sectional view of an example of a particle adsorption probe in a preferred embodiment of the present invention. In FIG. 1, a particle adsorption probe 1000 of the present invention consists only of a carbon nanotube aggregate 100 including a plurality of carbon nanotubes 10. In FIG. 1, the plurality of carbon nanotubes 10 are each aligned in the direction of a length L and constitute the bundle-like carbon nanotube aggregate 100.

Figure 2:
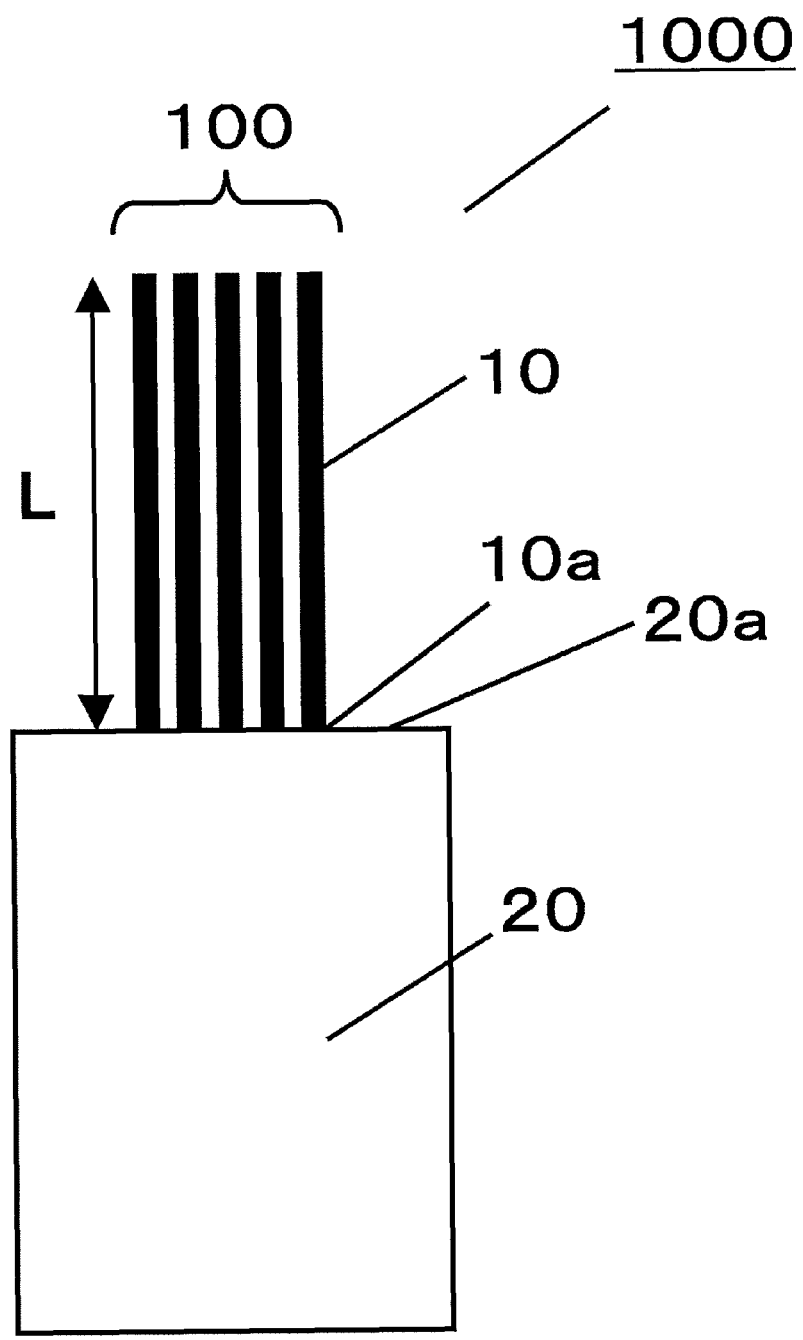
FIG. 2 is a schematic sectional view of another example of the particle adsorption probe in the preferred embodiment of the present invention.

FIG. 2 is a schematic sectional view of another example of the particle adsorption probe in the preferred embodiment of the present invention. In FIG. 2, in the particle adsorption probe 1000 of the present invention, the carbon nanotube aggregate 100 including the plurality of carbon nanotubes 10 is provided on a shaft-shaped base material 20. In FIG. 2, the plurality of carbon nanotubes 10 are each aligned in the direction of the length L and constitute the bundle-like carbon nanotube aggregate 100. In FIG. 2, one end 10a of each of the plurality of carbon nanotubes 10 is fixed onto the shaft-shaped base material 20. As illustrated in FIG. 2, the plurality of carbon nanotubes 10 are each preferably aligned in a direction substantially perpendicular to the shaft-shaped base material 20. The term "direction substantially perpendicular" as used herein means that the angle of the carbon nanotube with respect to a cross-section side surface 20a of the shaft-shaped base material 20 falls within the range of preferably 90 °±20°, more preferably 90°±15°, still more preferably 90°±10°, particularly preferably 90°±5°.

The particle adsorption probe of the present invention can selectively pick up a particle having a specific particle diameter from a group of particles having a wide particle diameter distribution, and preferably selectively adsorbs a particle having a diameter of 200 µm or less.

In the particle adsorption probe of the present invention, the carbon nanotube aggregate 100 has a length of preferably from 0.1 µm to 5,000 µm, more preferably from 1 µm to 2,000 µm, still more preferably from 10 µm to 1,000 µm, particularly preferably from 30 µm to 500 µm. When the length of the carbon nanotube aggregate 100 falls within the range, the particle adsorption probe of the present invention can more selectively pick up a particle having a specific particle diameter from a group of particles having a wide particle diameter distribution, and plastic deformation of the particle adsorption probe is alleviated. Accordingly, the particle adsorption probe can stably hold the picked-up particle. In addition, when the length of the carbon nanotube aggregate 100 falls within the range, the particle adsorption probe selectively adsorbs a particle having a diameter of preferably 200 µm or less.

In the particle adsorption probe of the present invention, the carbon nanotube aggregate 100 has a diameter of preferably from 0.1 µm to 2,000 µm, more preferably from 1 µm to 1,000 µm, still more preferably from 10 µm to 500 µm, particularly preferably from 20 µm to 300 µm. When the diameter of the carbon nanotube aggregate 100 falls within the range, the particle adsorption probe of the present invention can more selectively pick up a particle having a specific particle diameter from a group of particles having a wide particle diameter distribution, and plastic deformation of the particle adsorption probe is alleviated. Accordingly, the particle adsorption probe can stably hold the picked-up particle. In addition, when the diameter of the carbon nanotube aggregate 100 falls within the range, the particle adsorption probe selectively adsorbs a particle having a diameter of preferably 200 µm or less.

In the particle adsorption probe of the present invention, regarding the shape of each of the carbon nanotubes, the lateral section of the carbon nanotube has only to have any appropriate shape. The lateral section is of, for example, a substantially circular shape, an oval shape, or an n-gonal shape (n represents an integer of 3 or more).

In the particle adsorption probe of the present invention, the specific surface area and density of each of the carbon nanotubes may be set to any appropriate values.

Any appropriate material may be adopted as a material for the shaft-shaped base material depending on purposes. Although ruby, sapphire, and the like may be given as examples of such material, preferred examples of the material include conductive materials such as SUS and tungsten carbide.

Any appropriate size may be adopted as the size of the shaft-shaped base material depending on purposes. Such size is preferably as follows: the area of the cross-section side surface of the shaft-shaped base material is larger than an area calculated from the diameter of the carbon nanotube aggregate. It should be noted that any appropriate length may be adopted as the length of the shaft-shaped base material (length in a direction perpendicular to the cross-section side surface) depending on purposes.

When the particle adsorption probe of the present invention has a construction in which the carbon nanotube aggregate is provided on the shaft-shaped base material as illustrated in FIG. 2, any appropriate method may be adopted as a method of fixing the carbon nanotubes onto the shaft-shaped base material. Examples of such fixation method include: a method involving using a paste or the like to perform bonding; a method involving using a double-sided tape or the like to perform fixation based on pressure-sensitive adhesion; and a method involving using, as the shaft-shaped base material, a substrate used in the production of the carbon nanotube aggregate. Of those fixation methods, a method involving using a conductive material to perform fixation is preferred in order to prevent static buildup in consideration of the case where a particle is analytically evaluated in an analysis apparatus directly after the particle has been picked up, and specific examples thereof include: a method involving using a metal paste such as a Ag paste to perform bonding; and a method involving using a conductive double-sided tape to perform fixation based on pressure-sensitive adhesion.

<<Carbon Nanotube Aggregate>>

Regarding the carbon nanotube aggregate included in the particle adsorption probe of the present invention, two preferred embodiments as described below may be adopted.

<First Preferred Embodiment>

A preferred embodiment (hereinafter sometimes referred to as "first preferred embodiment") of the carbon nanotube aggregate included in the particle adsorption probe of the present invention includes a plurality of carbon nanotubes, in which the carbon nanotubes each have a plurality of walls, in which the distribution width of the wall number distribution of the carbon nanotubes is 10 walls or more, and in which the relative frequency of the mode of the wall number distribution is 25% or less.

The distribution width of the wall number distribution of the carbon nanotubes is 10 walls or more, preferably from 10 walls to 30 walls, more preferably from 10 walls to 25 walls, still more preferably from 10 walls to 20 walls.

The "distribution width" of the wall number distribution of the carbon nanotubes refers to a difference between the maximum wall number and minimum wall number in the wall numbers of the carbon nanotubes.

When the distribution width of the wall number distribution of the carbon nanotubes falls within the range, the carbon nanotubes can bring together excellent mechanical properties and a high specific surface area, and moreover, the carbon nanotubes can provide a carbon nanotube aggregate exhibiting excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

The wall numbers and wall number distribution of the carbon nanotubes may be measured with any appropriate device. The wall numbers and wall number distribution of the carbon nanotubes are preferably measured with a scanning electron microscope (SEM) or a transmission electron microscope (TEM). For example, at least 10, preferably 20 or more carbon nanotubes may be taken out from a carbon nanotube aggregate to evaluate the wall number and the wall number distribution by the measurement with the SEM or the TEM.

The maximum wall number of the carbon nanotubes is preferably from 5 to 30, more preferably from 10 to 30, still more preferably from 15 to 30, particularly preferably from 15 to 25.

The minimum wall number of the carbon nanotubes is preferably from 1 to 10, more preferably from 1 to 5.

When the maximum wall number and minimum wall number of the carbon nanotubes fall within the ranges, the carbon nanotubes can bring together additionally excellent mechanical properties and a high specific surface area, and moreover, the carbon nanotubes can provide a carbon nanotube aggregate exhibiting additionally excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

The relative frequency of the mode of the wall number distribution is 25% or less, preferably from 1% to 25%, more preferably from 5% to 25%, still more preferably from 10% to 25%, particularly preferably from 15% to 25%. When the relative frequency of the mode of the wall number distribution falls within the range, the carbon nanotubes can bring together excellent mechanical properties and a high specific surface area, and moreover, the carbon nanotubes can provide a carbon nanotube aggregate exhibiting excellent pressure-sensitive adhesive property. Therefore, the particle adsorption probe using such carbon nanotube aggregate does not require the application of a physical stress in picking up a particle, does not contaminate a foreign matter surface in picking up the particle, can more selectively pick up a particle having a specific particle diameter from a group of particles having a wide particle diameter distribution, and allows the particle to be analytically evaluated in an analysis apparatus directly after picking up the particle.

The mode of the wall number distribution is present at preferably from 2 to 10 walls in number, more preferably from 3 to 10 walls in number. When the mode of the wall number distribution falls within the range, the carbon nanotubes can bring together excellent mechanical properties and a high specific surface area, and moreover, the carbon nanotubes can provide a carbon nanotube aggregate exhibiting excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

<Second Preferred Embodiment>

Another preferred embodiment (hereinafter sometimes referred to as "second preferred embodiment") of the carbon nanotube aggregate included in the particle adsorption probe of the present invention includes a plurality of carbon nanotubes, in which the carbon nanotubes each have a plurality of walls, in which the mode of the wall number distribution of the carbon nanotubes is present at 10 or less walls in number, and in which the relative frequency of the mode is 30% or more.

The distribution width of the wall number distribution of the carbon nanotubes is preferably 9 walls or less, more preferably from 1 walls to 9 walls, still more preferably from 2 walls to 8 walls, particularly preferably from 3 walls to 8 walls.

The "distribution width" of the wall number distribution of the carbon nanotubes refers to a difference between the maximum wall number and minimum wall number of the wall numbers of the carbon nanotubes.

When the distribution width of the wall number distribution of the carbon nanotubes falls within the range, the carbon nanotubes can bring together excellent mechanical properties and a high specific surface area, and moreover, the carbon nanotubes can provide a carbon nanotube aggregate exhibiting excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

The wall numbers and wall number distribution of the carbon nanotubes may be measured with any appropriate device. The wall numbers and wall number distribution of the carbon nanotubes are preferably measured with a scanning electron microscope (SEM) or a transmission electron microscope (TEM). For example, at least 10, preferably 20 or more carbon nanotubes may be taken out from a carbon nanotube aggregate to evaluate the wall numbers and the wall number distribution by the measurement with the SEM or the TEM.

The maximum wall number of the carbon nanotubes is preferably from 1 to 20, more preferably from 2 to 15, still more preferably from 3 to 10.

The minimum wall number of the carbon nanotubes is preferably from 1 to 10, more preferably from 1 to 5.

When the maximum wall number and minimum wall number of the carbon nanotubes fall within the ranges, the carbon nanotubes can bring together additionally excellent mechanical properties and a high specific surface area, and moreover, the carbon nanotubes can provide a carbon nanotube aggregate exhibiting additionally excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

The relative frequency of the mode of the wall number distribution is 30% or more, preferably from 30% to 100%, more preferably from 30% to 90%, still more preferably from 30% to 80%, particularly preferably from 30% to 70%. When the relative frequency of the mode of the wall number distribution falls within the range, the carbon nanotubes can bring together excellent mechanical properties and a high specific surface area, and moreover, the carbon nanotubes can provide a carbon nanotube aggregate exhibiting excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

The mode of the wall number distribution is present at 10 or less walls in number, preferably from 1 to 10 walls in number, more preferably from 2 to 8 walls in number, still more preferably from 2 to 6 walls in number. In the present invention, when the mode of the wall number distribution falls within the range, the carbon nanotubes can bring together excellent mechanical properties and a high specific surface area, and moreover, the carbon nanotubes can provide a carbon nanotube aggregate exhibiting excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

<<Method of Producing Carbon Nanotube Aggregate>>

Any appropriate method may be adopted as a method of producing the carbon nanotube aggregate included in the particle adsorption probe of the present invention.

The method of producing the carbon nanotube aggregate included in the particle adsorption probe of the present invention is, for example, a method of producing a carbon nanotube aggregate aligned substantially perpendicularly from a smooth substrate by chemical vapor deposition (CVD) involving forming a catalyst layer on the substrate and filling a carbon source in a state in which a catalyst is activated with heat, plasma, or the like to grow the carbon nanotubes. In this case, for example, the removal of the substrate provides a carbon nanotube aggregate aligned in a lengthwise direction.

Any appropriate substrate may be adopted as the substrate. The substrate is, for example, a material having smoothness and high-temperature heat resistance enough to resist the production of the carbon nanotubes. Examples of such material include quartz glass, silicon (such as a silicon wafer), and a metal plate made of, for example, aluminum. The substrate may be directly used as the shaft-shaped base material that may be included in the particle adsorption probe of the present invention.

Figure 3:
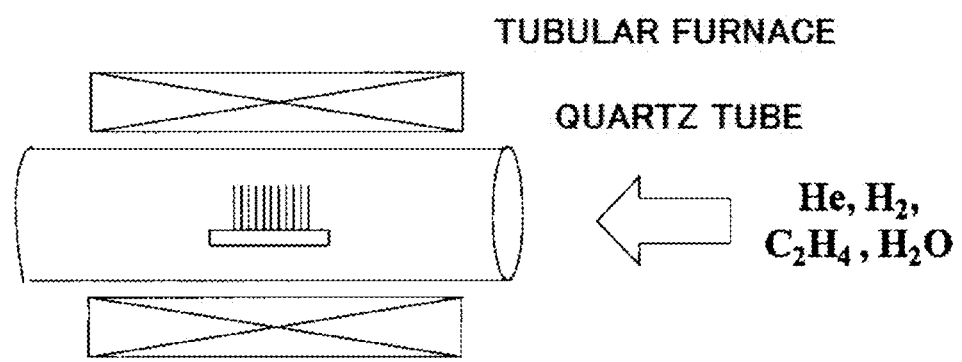
FIG. 3 is a schematic sectional view of an apparatus for producing a carbon nanotube aggregate in the preferred embodiment of the present invention.

Any appropriate apparatus may be adopted as an apparatus for producing the carbon nanotube aggregate included in the particle adsorption probe of the present invention. The apparatus is, for example, a thermal CVD apparatus of a hot wall type formed by surrounding a cylindrical reaction vessel with a resistance heating electric tubular furnace as illustrated in FIG. 3. In this case, for example, a heat-resistant quartz tube is preferably used as the reaction vessel.

Any appropriate catalyst may be used as the catalyst (material for the catalyst layer) that may be used in the production of the carbon nanotube aggregate included in the particle adsorption probe of the present invention. Examples of the catalyst include metal catalysts such as iron, cobalt, nickel, gold, platinum, silver, and copper.

Upon production of the carbon nanotube aggregate included in the particle adsorption probe of the present invention, an alumina/hydrophilic film may be formed between the substrate and the catalyst layer as required.

Any appropriate method may be adopted as a method of producing the alumina/hydrophilic film. For example, the film may be obtained by producing a $SiO_2$ film on the substrate, depositing Al from the vapor, and increasing the temperature of Al to 450° C. after the deposition to oxidize Al. According to such production method, $Al_2O_3$ interacts with the hydrophilic $SiO_2$ film, and hence an $Al_2O_3$ surface different from that obtained by directly depositing $Al_2O_3$ from the vapor in particle diameter is formed. When Al is deposited from the vapor, and then its temperature is increased to 450° C. so that Al may be oxidized without the production of any hydrophilic film on the substrate, it may be difficult to form the $Al_2O_3$ surface having a different particle diameter. In addition, when the hydrophilic film is produced on the substrate and $Al_2O_3$ is directly deposited from the vapor, it may also be difficult to form the $Al_2O_3$ surface having a different particle diameter.

The catalyst layer that may be used in the production of the carbon nanotube aggregate included in the particle adsorption probe of the present invention has a thickness of preferably from 0.01 nm to 20 nm, more preferably from 0.1 nm to 10 nm in order that fine particles may be formed. When the thickness of the catalyst layer that may be used in the production of the carbon nanotube aggregate included in the particle adsorption probe of the present invention falls within the range, the carbon nanotube aggregate can bring together excellent mechanical properties and a high specific surface area, and moreover, the carbon nanotube aggregate can exhibit excellent pressure-sensitive adhesive property. Therefore, the particle adsorption probe using such carbon nanotube aggregate can selectively pick up a particle having a specific particle diameter from a group of particles having a wide particle diameter distribution without requiring the application of a physical stress in picking up the particle and without contaminating a foreign matter surface in picking up the particle, and allows the particle to be analytically evaluated in an analysis apparatus directly after picking up the particle.

Any appropriate method may be adopted as a method of forming the catalyst layer. Examples of the method include a method involving depositing a metal catalyst from the vapor, for example, with an electron beam (EB) or by sputtering and a method involving applying a suspension of metal catalyst fine particles onto the substrate.

After its formation, the catalyst layer may be processed by a photolithographic process so as to have a pattern having any appropriate diameter. When such photolithographic process is performed, a carbon nanotube aggregate having a desired diameter can be produced in the end.

Any appropriate carbon source may be used as the carbon source that may be used in the production of the carbon nanotube aggregate included in the particle adsorption probe of the present invention. Examples thereof include: hydrocarbons such as methane, ethylene, acetylene, and benzene; and alcohols such as methanol and ethanol.

Any appropriate temperature may be adopted as a production temperature in the production of the carbon nanotube aggregate included in the particle adsorption probe of the present invention. For example, the temperature is preferably from 400° C. to 1,000° C., more preferably from 500° C. to 900° C., still more preferably from 600° C. to 800° C. in order that catalyst particles allowing sufficient expression of the effects of the present invention may be formed.

EXAMPLES

Hereinafter, the present invention is described by way of Examples. However, the present invention is not limited thereto. It should be noted that various evaluations and measurements were performed by the following methods.
<Measurement of Length and Diameter of Carbon Nanotube Aggregate>

The length and diameter of a carbon nanotube aggregate were measured with a scanning electron microscope (SEM).
<Evaluation of Wall Numbers and Wall Number Distribution of Carbon Nanotubes in Carbon Nanotube Aggregate>

The wall numbers and wall number distribution of carbon nanotubes in the carbon nanotube aggregate were measured with a scanning electron microscope (SEM) and/or a transmission electron microscope (TEM). At least 10 or more, preferably 20 or more carbon nanotubes in the obtained carbon nanotube aggregate were observed with the SEM and/or the TEM to check the wall number of each carbon nanotube, and the wall number distribution was created.
<Probe Test>

The carbon nanotube aggregate was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

The obtained particle adsorption probe was fixed onto a sampling machine AxisPro (manufactured by Micro Support Co., Ltd.) and brought into contact with glass beads having various particle diameters shown below (FUJI GLASS BEADS (manufactured by Fuji Manufacturing Co., Ltd.). Then, a particle adsorption state was examined without applying a stress. A case where a particle was adsorbed was marked with Symbol "o", and a case where no particle was adsorbed was marked with Symbol "x".
FGB-1500: particle diameter: 20 μm or less
FGB-1000: particle diameter: 30 μm or less
FGB-320: particle diameter: 38 μm to 53 μm
FGB-120: particle diameter: 125 μm to 150 μm
FGB-60: particle diameter: 250 μm to 355 μm Example 1

An Al thin film (thickness: 5 nm) was formed on a silicon wafer (manufactured by Silicon Technology Co., Ltd.) as a substrate with a sputtering apparatus (RFS-200 manufactured by ULVAC, Inc.). An Fe thin film (thickness: 0.35 nm) was further deposited from the vapor onto the Al thin film with the sputtering apparatus (RFS-200 manufactured by ULVAC, Inc.). After that, a pattern having a diameter of 30 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 0.5 minute to grow carbon nanotubes on the substrate. Thus, a carbon nanotube aggregate (1) in which the carbon nanotubes were aligned in their length direction was obtained.

The carbon nanotube aggregate (1) had a length of 10 μm and a diameter of 30 μm.

In the wall number distribution of the carbon nanotubes included in the carbon nanotube aggregate (1), a mode was present at 1 wall, and its relative frequency was 61%.

The obtained carbon nanotube aggregate (1) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 2

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 1 nm) was further deposited from the vapor onto the alumina thin film with the sputtering apparatus (RFS-200 manufactured by ULVAC, Inc.). After that, a pattern having a diameter of 20 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 2.5 minutes to grow carbon nanotubes on the substrate. Thus, a carbon nanotube aggregate (2) in which the carbon nanotubes were aligned in their length direction was obtained.

The carbon nanotube aggregate (2) had a length of 30 μm and a diameter of 20 μm.

In the wall number distribution of the carbon nanotubes included in the carbon nanotube aggregate (2), a mode was present at 2 walls, and its relative frequency was 75%.

The obtained carbon nanotube aggregate (2) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 3

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 1 nm) was further deposited from the vapor onto the alumina thin film with the sputtering apparatus (RFS-200 manufactured by ULVAC, Inc.). After that, a pattern having a diameter of 60 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 2.5 minutes to grow carbon nanotubes on the substrate. Thus, a carbon nanotube aggregate (3) in which the carbon nanotubes were aligned in their length directions was obtained.

The carbon nanotube aggregate (3) had a length of 30 μm and a diameter of 60 μm.

In the wall number distribution of the carbon nanotubes included in the carbon nanotube aggregate (3), a mode was present at 2 walls, and its relative frequency was 75%.

The obtained carbon nanotube aggregate (3) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Figure 4:
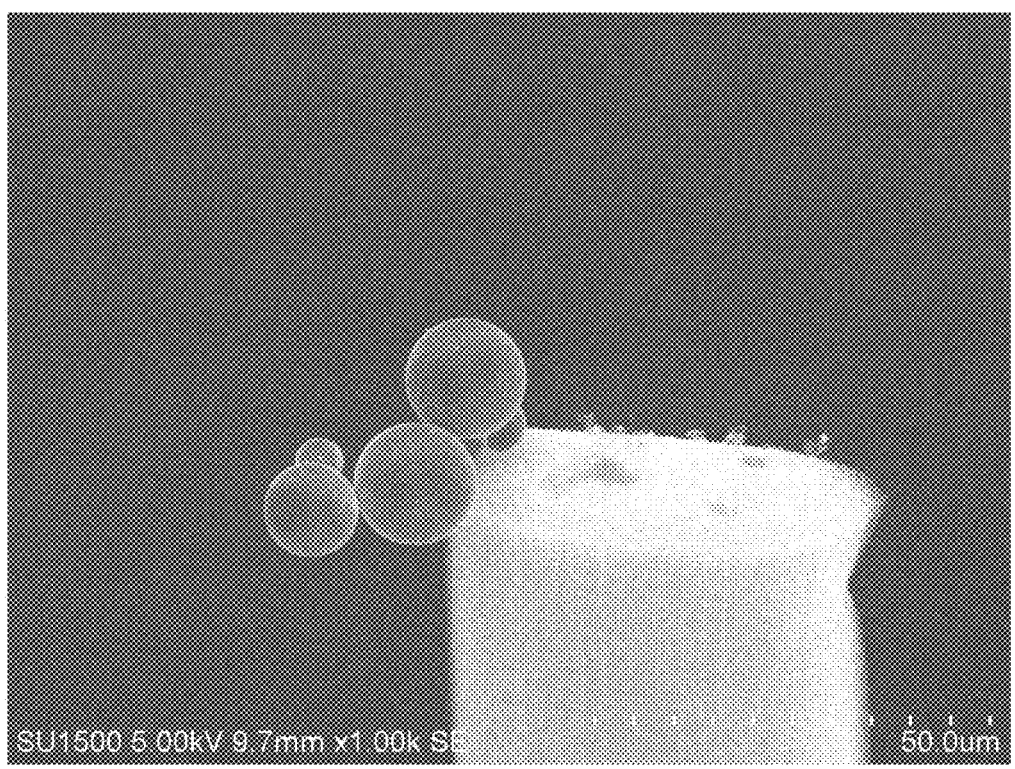
FIG. 4 is a photographic view taken with a scanning electron microscope (SEM), showing a state in which particles are adsorbed onto a particle adsorption probe obtained in Example 3.

In addition, FIG. 4 shows a photographic view taken with a scanning electron microscope (SEM), showing a state in which particles are adsorbed onto the obtained particle adsorption probe.

Example 4

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 1 nm) was further deposited from the vapor onto the alumina thin film with the sputtering apparatus (RFS-200 manufactured by ULVAC, Inc.). After that, a pattern having a diameter of 150 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 2.5 minutes to grow carbon nanotubes on the substrate. Thus, a carbon nanotube aggregate (4) in which the carbon nanotubes were aligned in their length direction was obtained.

The carbon nanotube aggregate (4) had a length of 30 μm and a diameter of 150 μm.

In the wall number distribution of the carbon nanotubes included in the carbon nanotube aggregate (4), a mode was present at 2 walls, and its relative frequency was 75%.

The obtained carbon nanotube aggregate (4) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 5

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 2 nm) was further deposited from the vapor onto the alumina thin film with the sputtering apparatus (RFS-200 manufactured by ULVAC, Inc.). After that, a pattern having a diameter of 20 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 4 minutes to grow carbon nanotubes on the substrate. Thus, a carbon nanotube aggregate (5) in which the carbon nanotubes were aligned in their length direction was obtained.

The carbon nanotube aggregate (5) had a length of 50 µm and a diameter of 20 µm.

In the wall number distribution of the carbon nanotubes included in the carbon nanotube aggregate (5), a mode was present at 3 walls, and its relative frequency was 72%.

The obtained carbon nanotube aggregate (5) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 6

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 2 nm) was further deposited from the vapor onto the alumina thin film with the sputtering apparatus (RFS-200 manufactured by ULVAC, Inc.). After that, a pattern having a diameter of 60 µm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 4 minutes to grow carbon nanotubes on the substrate. Thus, a carbon nanotube aggregate (6) in which the carbon nanotubes were aligned in their length direction was obtained.

The carbon nanotube aggregate (6) had a length of 50 µm and a diameter of 60 µm.

In the wall number distribution of the carbon nanotubes included in the carbon nanotube aggregate (6), a mode was present at 3 walls, and its relative frequency was 72%.

The obtained carbon nanotube aggregate (6) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 7

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 2 nm) was further deposited from the vapor onto the alumina thin film with the sputtering apparatus (RFS-200 manufactured by ULVAC, Inc.). After that, a pattern having a diameter of 150 µm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 4 minutes to grow carbon nanotubes on the substrate. Thus, a carbon nanotube aggregate (7) in which the carbon nanotubes were aligned in their length direction was obtained.

The carbon nanotube aggregate (7) had a length of 50 µm and a diameter of 150 µm.

In the wall number distribution of the carbon nanotubes included in the carbon nanotube aggregate (7), a mode was present at 3 walls, and its relative frequency was 72%.

The obtained carbon nanotube aggregate (7) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 8

An Al thin film (thickness: 10 nm) was formed on a silicon substrate (manufactured by KST, wafer with a thermal oxide film, thickness: 1,000 µm) with a vacuum deposition apparatus (JEE-4X Vacuum Evaporator manufactured by JEOL Ltd.). After that, the resultant was subjected to oxidation treatment at 450° C. for 1 hour. Thus, an $Al_2O_3$ film was formed on the silicon substrate. An Fe thin film (thickness: 2 nm) was further deposited from the vapor onto the $Al_2O_3$ film with a sputtering apparatus (RFS-200 manufactured by ULVAC, Inc.) to form a catalyst layer. After that, a pattern having a diameter of 200 µm was formed by a photolithographic process.

Next, the obtained silicon substrate with the catalyst layer was cut and mounted in a quartz tube having a diameter of 30 mm, and a helium/hydrogen (120/80 sccm) mixed gas whose moisture content had been held at 350 ppm was flowed into the quartz tube for 30 minutes to replace the inside of the tube. After that, a temperature in the tube was increased with an electric tubular furnace to 765° C. in 35 minutes in a stepwise manner, and was stabilized at 765° C. While the temperature was held at 765° C., the inside of the tube was filled with a helium/hydrogen/ethylene (105/80/15 sccm, moisture content: 350 ppm) mixed gas, and the resultant was left to stand for 20 minutes to grow carbon nanotubes on the substrate. Thus, a carbon nanotube aggregate (8) in which the carbon nanotubes were aligned in their length directions was obtained.

The carbon nanotube aggregate (8) had a length of 400 µm and a diameter of 200 µm.

In the wall number distribution of the carbon nanotubes included in the carbon nanotube aggregate (8), the distribution width of the wall number distribution was 17 walls (4 walls to 20 walls), modes were present at 4 walls and 8 walls, and their relative frequencies were 20% and 20%, respectively.

The obtained carbon nanotube aggregate (8) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 9

An Al thin film (thickness: 5 nm) was formed on a silicon wafer (manufactured by Silicon Technology Co., Ltd.) as a substrate with a sputtering apparatus (RFS-200 manufactured by ULVAC, Inc.). An Fe thin film (thickness: 0.35 nm) was further deposited from the vapor onto the Al thin film with the sputtering apparatus (RFS-200 manufactured by ULVAC, Inc.). After that, a pattern having a diameter of 10 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 0.5 minute to grow carbon nanotubes on the substrate. Thus, a carbon nanotube aggregate (9) in which the carbon nanotubes were aligned in their length direction was obtained.

The carbon nanotube aggregate (9) had a length of 10 μm and a diameter of 10 μm.

In the wall number distribution of the carbon nanotubes included in the carbon nanotube aggregate (9), a mode was present at 1 wall, and its relative frequency was 61%.

The obtained carbon nanotube aggregate (9) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 10

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 1 nm) was further deposited from the vapor onto the alumina thin film with the sputtering apparatus (RFS-200 manufactured by ULVAC, Inc.). After that, a pattern having a diameter of 10 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 2.5 minutes to grow carbon nanotubes on the substrate. Thus, a carbon nanotube aggregate (10) in which the carbon nanotubes were aligned in their length direction was obtained.

The carbon nanotube aggregate (10) had a length of 30 μm and a diameter of 10 μm.

In the wall number distribution of the carbon nanotubes included in the carbon nanotube aggregate (10), a mode was present at 2 walls, and its relative frequency was 75%.

The obtained carbon nanotube aggregate (10) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Example 11

An alumina thin film (thickness: 20 nm) was formed on a silicon wafer (manufactured by Silicon Technology Co., Ltd.) as a substrate with a sputtering apparatus (RFS-200 manufactured by ULVAC, Inc.). An Fe thin film (thickness: 2 nm) was further deposited from the vapor onto the alumina thin film with the sputtering apparatus (RFS-200 manufactured by ULVAC, Inc.). After that, a pattern having a diameter of 10 μm was formed by a photolithographic process.

After that, the substrate was mounted in a quartz tube having a diameter of 30 mm, and a helium/hydrogen (90/50 sccm) mixed gas whose moisture content had been held at 600 ppm was flowed into the quartz tube for 30 minutes to replace the inside of the tube. After that, a temperature in the tube was increased with an electric tubular furnace to 765° C. and stabilized at 765° C. While the temperature was held at 765° C., the inside of the tube was filled with a helium/hydrogen/ethylene (85/50/5 sccm, moisture content: 600 ppm) mixed gas, and the resultant was left to stand for 4 minutes to grow carbon nanotubes on the substrate. Thus, a carbon nanotube aggregate (11) in which the carbon nanotubes were aligned in their length direction was obtained.

The carbon nanotube aggregate (11) had a length of 50 μm and a diameter of 10 μm.

In the wall number distribution of the carbon nanotubes included in the carbon nanotube aggregate (11), a mode was present at 3 walls, and its relative frequency was 72%.

The obtained carbon nanotube aggregate (11) was bonded onto a smooth cross-section of a tungsten needle (diameter: 0.7 mm) through the use of a silver paste (DOTITE D362, manufactured by Fujikura Kasei Co., Ltd.), to thereby produce a particle adsorption probe.

Table 1 shows evaluation results.

Comparative Example 1

Evaluation was performed using a tungsten probe (TP-010, manufactured by Micro Support Co., Ltd.) as a particle adsorption probe.

Table 1 shows evaluation results.

Comparative Example 2

Evaluation was performed using a tungsten probe (TP-030, manufactured by Micro Support Co., Ltd.) as a particle adsorption probe.

Table 1 shows evaluation results.

TABLE 1

| | | Length of CNT aggregate μm | Diameter of CNT aggregate μm | Probe test | | | | |
|---|---|---|---|---|---|---|---|---|
| | | | | FGB-1500 ≤20 μm | FGB-1000 ≤30 μm | FGB-320 38 μm to 53 μm | FGB-120 125 μm to 150 μm | FGB-60 250 μm to 355 μm |
| Example 1 | SW-61 | 10 | 30 | ○ | ○ | x | x | x |
| Example 2 | DW-75 | 30 | 20 | ○ | ○ | x | x | x |
| Example 3 | DW-75 | 30 | 60 | ○ | ○ | ○ | x | x |

TABLE 1-continued

| | | Length of CNT aggregate μm | Diameter of CNT aggregate μm | Probe test | | | | |
|---|---|---|---|---|---|---|---|---|
| | | | | FGB-1500 ≤20 μm | FGB-1000 ≤30 μm | FGB-320 38 μm to 53 μm | FGB-120 125 μm to 150 μm | FGB-60 250 μm to 355 μm |
| Example 4 | DW-75 | 30 | 150 | ○ | ○ | ○ | x | x |
| Example 5 | TW-72 | 50 | 20 | ○ | ○ | x | x | x |
| Example 6 | TW-72 | 50 | 60 | ○ | ○ | ○ | x | x |
| Example 7 | TW-72 | 50 | 150 | ○ | ○ | ○ | ○ | x |
| Example 8 | Broad | 400 | 200 | ○ | ○ | ○ | ○ | x |
| Example 9 | SW-61 | 10 | 10 | ○ | x | x | x | x |
| Example 10 | DW-75 | 30 | 10 | ○ | x | x | x | x |
| Example 11 | TW-72 | 50 | 10 | ○ | x | x | x | x |
| Comparative Example 1 | Tungsten probe (diameter: 10 μm) | | | x | x | x | x | x |
| Comparative Example 2 | Tungsten probe (diameter: 30 μm) | | | x | x | x | x | x |

As apparent from Table 1, each of the particle adsorption probes obtained in Examples can selectively pick up particles each having a specific particle diameter from a group of particles having a wide particle diameter distribution without requiring the application of a physical stress in picking up the particles and without contaminating a foreign matter surface in picking up the particles.

Example 12

The particle adsorption probe obtained in Example 3 was able to maintain the state shown in the photographic view of FIG. 4, taken with a scanning electron microscope (SEM), in the analysis apparatus directly after picking up particles.

Thus, it was found that the particle adsorption probe obtained in Example 3 allowed the particles to be analytically evaluated in the analysis apparatus directly after picking up the particles.

INDUSTRIAL APPLICABILITY

The particle adsorption probe of the present invention is suitably used for, for example, picking up fine particles scattered on a surface of an object to be analyzed in an analysis application or the like so that the particles may be carried into an analysis apparatus and analytically evaluated.

REFERENCE SIGNS LIST

1000 particle adsorption probe
100 carbon nanotube aggregate
10 carbon nanotube
10a one end of carbon nanotube
20 shaft-shaped base material
20a cross-section side surface of shaft-shaped base material

The invention claimed is:

1. A particle adsorption probe, comprising a carbon nanotube aggregate including a plurality of carbon nanotubes,
   wherein the carbon nanotube aggregate has diameter of from 10 μm to 500 μm.

2. The particle adsorption probe according to claim 1, wherein the particle adsorption probe selectively adsorbs a particle having a diameter of 200 μm or less.

3. The particle adsorption probe according to claim 1, further comprising a shaft-shaped base material, wherein the carbon nanotube aggregate is provided on the shaft-shaped base material.

4. The particle adsorption probe according to claim 3, wherein the shaft-shaped base material comprises at least one material selected from the group consisting of ruby, sapphire, stainless steel, and tungsten carbide.

5. The particle adsorption probe according to claim 1,
   wherein the carbon nanotubes each have a plurality of walls,
   wherein a distribution width of a wall number distribution of the carbon nanotubes is 10 walls or more, and
   wherein a relative frequency of a mode of the wall number distribution is 25% or less.

6. The particle adsorption probe according to claim 1,
   wherein the carbon nanotubes each have a plurality of walls,
   wherein a mode of a wall number distribution of the carbon nanotubes is present at 10 or less walls in number, and
   wherein a relative frequency of the mode is 30% or more.

7. The particle adsorption probe according to claim 6, wherein a distribution width of the wall number distribution of the carbon nanotubes is from 1 to 9 walls.

8. The particle adsorption probe according to claim 6, wherein a distribution width of the wall number distribution of the carbon nanotubes is from 3 to 8 walls.

9. The particle adsorption probe according to claim 6, wherein a maximum wall number of the carbon nanotubes is from 2 to 20.

10. The particle adsorption probe according to claim 6, wherein a maximum wall number of the carbon nanotubes is from 3 to 10.

* * * * *